United States Patent
Poyner et al.

(10) Patent No.: US 7,303,563 B2
(45) Date of Patent: Dec. 4, 2007

(54) ORTHOPEDIC FIXATION SYSTEM AND METHOD OF USE

(75) Inventors: Jeffrey W. Poyner, Bartlett, TN (US); Robert A. Farris, Cordova, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 10/870,504

(22) Filed: Jun. 17, 2004

(65) Prior Publication Data

US 2005/0283153 A1 Dec. 22, 2005

(51) Int. Cl.
- *A61B 17/56* (2006.01)
- *A61B 17/58* (2006.01)
- *A61F 2/30* (2006.01)

(52) U.S. Cl. .................................................. 606/61
(58) Field of Classification Search ............... None
See application file for complete search history.

(56) References Cited

U.S. PATENT DOCUMENTS

| | | | |
|---|---|---|---|
| 5,133,717 A | 7/1992 | Chopin | |
| 5,312,044 A | 5/1994 | Eaton | |
| 5,360,429 A | 11/1994 | Jeanson et al. | |
| 5,487,744 A | 1/1996 | Howland | |
| 5,545,164 A | 8/1996 | Howland | |
| 5,713,898 A | 2/1998 | Stucker et al. | |
| 5,800,435 A | 9/1998 | Errico et al. | |
| 5,925,047 A * | 7/1999 | Errico et al. ............... | 606/65 |
| 5,928,233 A | 7/1999 | Apfelbaum et al. | |
| 5,976,135 A | 11/1999 | Sherman et al. | |
| 6,106,526 A | 8/2000 | Harms et al. | |
| 6,129,730 A * | 10/2000 | Bono et al. ................ | 606/73 |
| 6,248,105 B1 * | 6/2001 | Schlapfer et al. .......... | 606/61 |
| 6,328,740 B1 | 12/2001 | Richelsoph | |
| 6,402,752 B2 | 6/2002 | Scäffler-Wachter et al. | |
| 6,485,491 B1 | 11/2002 | Farris et al. | |
| 6,524,315 B1 | 2/2003 | Selvitelli et al. | |
| 6,547,790 B2 | 4/2003 | Harkey, III et al. | |
| 6,572,622 B1 | 6/2003 | Schafer et al. | |
| 6,682,532 B2 | 1/2004 | Johnson et al. | |
| 7,022,122 B2 | 4/2006 | Amrein et al. | |
| 2002/0049446 A1 | 4/2002 | Harkey, III et al. | |
| 2003/0149432 A1 | 8/2003 | Frigg et al. | |
| 2003/0153913 A1 | 8/2003 | Altarac et al. | |
| 2004/0039396 A1 | 2/2004 | Couture et al. | |
| 2005/0165400 A1 * | 7/2005 | Fernandez ................. | 606/69 |

FOREIGN PATENT DOCUMENTS

DE 43 16 541 C 1 8/1994
FR 2 856 271 A 12/2004

* cited by examiner

*Primary Examiner*—William H. Matthews
(74) *Attorney, Agent, or Firm*—Coats & Bennett, P.L.L.C.

(57) ABSTRACT

A orthopedic fixation system comprising a plate with an outwardly-extending member. A saddle may be mounted on the member and includes spaced-apart arms that form a channel to receive a rod. An engagement member may be mounted within the saddle to prevent escape of the rod. In one embodiment, the engagement member is attached to the saddle to apply a downward force on the rod and an upward force on the saddle to lift the saddle relative to the plate. A method of attaching an orthopedic rod is also included. In one embodiment, a rod is positioned within a channel in the saddle and a downward force is applied against the anchor which results in an upward force on the saddle to lift the saddle relative to the anchor.

37 Claims, 9 Drawing Sheets

ORTHOPEDIC FIXATION SYSTEM AND METHOD OF USE

BACKGROUND

Orthopedic procedures often use implant systems that attach to one or more bones. The implants facilitate stabilization, and positioning of both injured bones, and also prevent further injuries from occurring in the future. The implant systems often include multiple separate pieces that work in combination. A first set of pieces is bone attachment mechanisms that attach to the bone, and a second set of pieces comprising elongated members that span an extended distance. The combination of the first and second sets provides attachment to the bone, and stabilization and positioning over two or more bones. One issue with the implant systems is attaching together the first and second sets.

One type of bone attachment mechanism is a fixation plate. The plate is sized to extend across one or more bones. One or more apertures extend through the plate and are sized to receive a bone screw. The plate is positioned with the aperture over the bone such that a screw can be inserted through the aperture to fixedly attach the plate. In most embodiments, apertures are positioned across the plate and screws are inserted to securely attach the plate to the bone and prevent movement of the plate.

Elongated members, such as rods, are sized to extend across two or more bones. The rods usually have a substantially round cross-sectional shape, and may include straight and curved sections depending upon the configuration of the bones to which they are to be attached. The rods are positioned in a manner to extend across the various bone regions for stabilization and support.

A difficultly in using the fixation systems is attaching the elongated members to the fixation plates. The position of the fixation plates and the elongated members is often dictated by the shape of the bones, and the location of the injury. Therefore, it is often difficult for a surgeon to accurately place the fixation plates and the elongated members in the required position that allows for the sets to be attached together.

SUMMARY

The present invention is directed to a fixation system for attaching elongated members to fixation plates. The system comprises a plate having at least one outwardly-extending anchor. The anchor may be integral with the plate or separately attached to the plate. A saddle is attached to the anchor at a position above the plate. The saddle includes arms that are spaced a distance apart to form a channel for receiving the elongated member. An engagement member is attached to the saddle at a point above the rod.

Various methods of attaching the orthopedic rod to the bone are also disclosed. One method includes threading the engagement member within the channel and applying a downward force on the rod against the anchor. A resultant upward force occurs on the saddle and lifts the saddle relative to the anchor.

DETAILED DESCRIPTION

The present invention is directed to an orthopedic device adapted to receive and support a rod using an adjustable coupling. Various embodiments will now be described with reference to the Figures where corresponding parts are referenced throughout this description by similar numbers.

Figure 1:
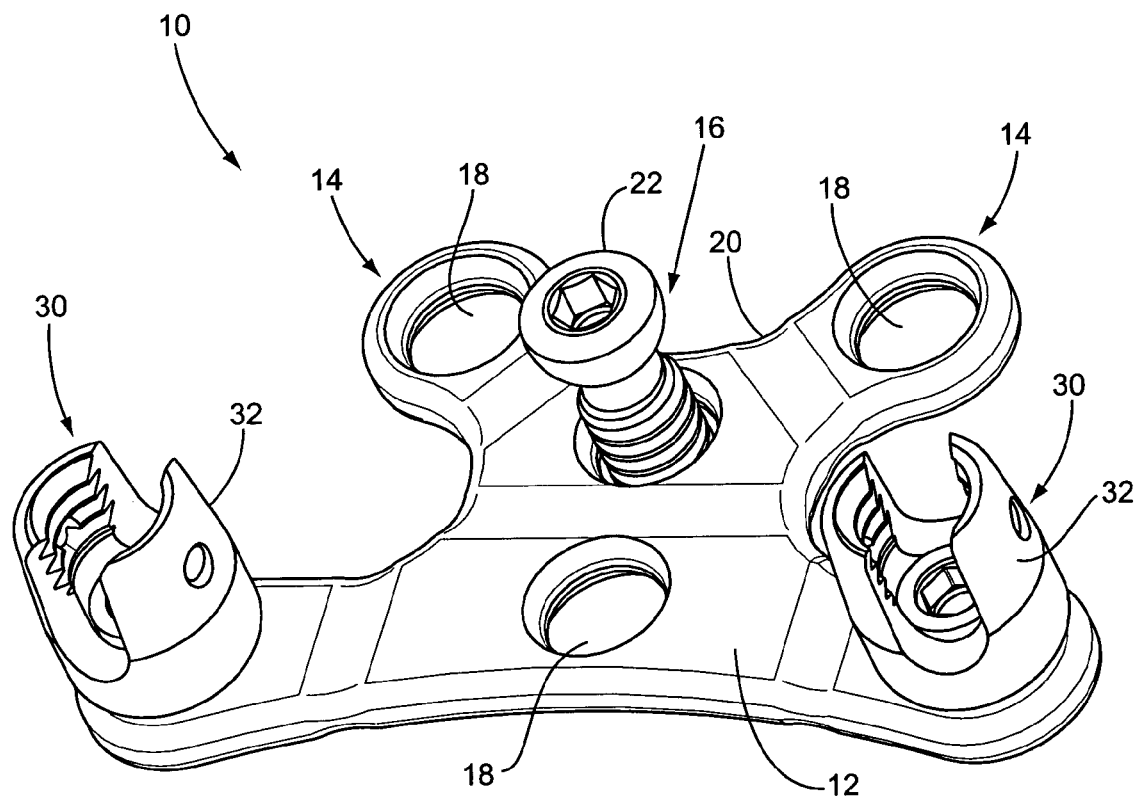
FIG. 1 is a perspective view of an occipital fixation system according to one embodiment of the present invention.
Figure 2:
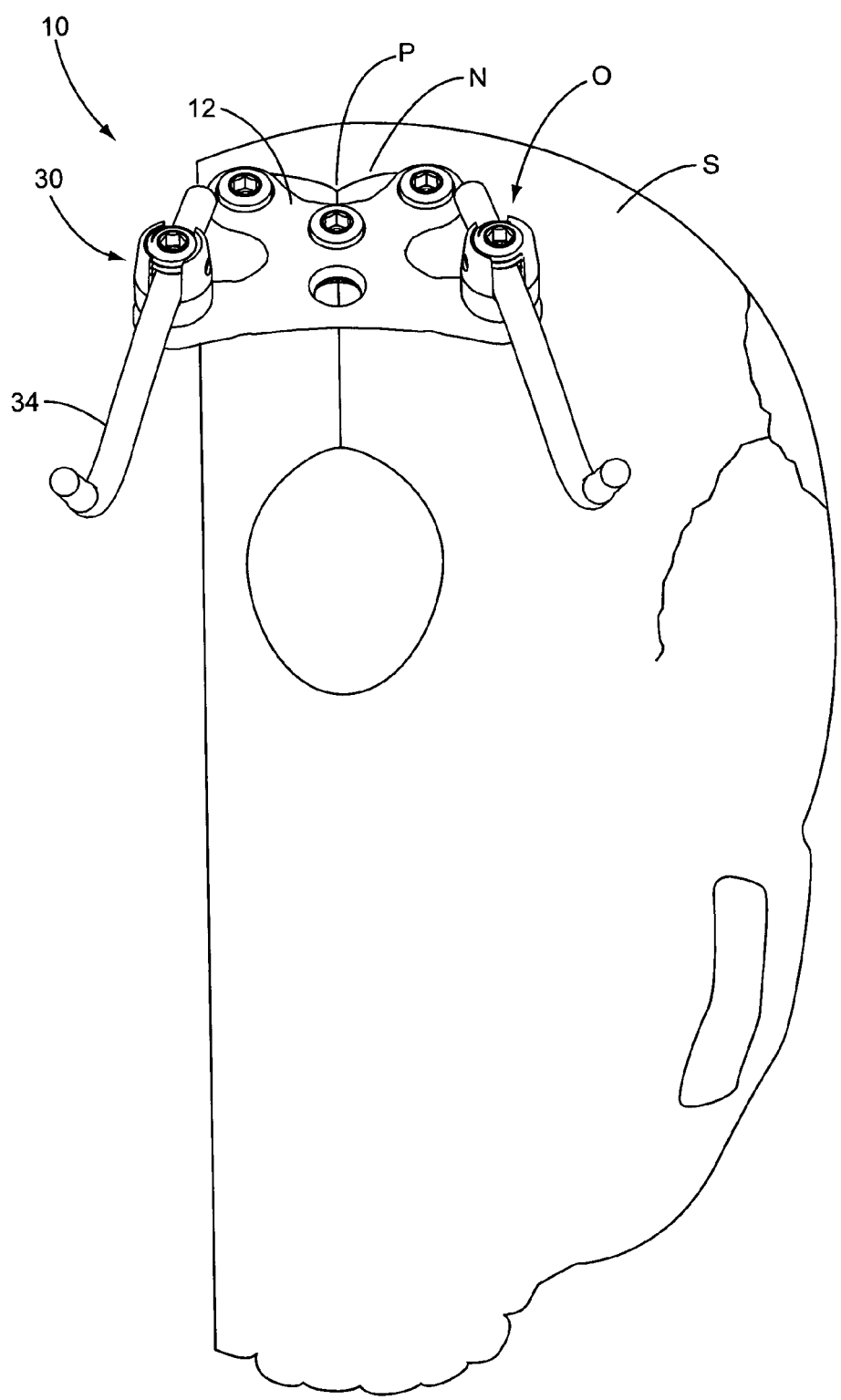
FIG. 2 is an schematic illustration of an inferior view of an occipital fixation system according to one embodiment of the present invention approximately positioned for attachment to a human skull.

In one embodiment, the invention is part of an occipital fixation system, designated generally by the number 10, as shown in FIGS. 1 and 2. FIG. 1 shows a perspective view of the fixation system 10. FIG. 2 shows a schematic of an inferior view of a human skull S with the fixation system 10 attached to the occipital bone O. The fixation system 10 comprises a plate 12 that has first and second outwardly extending sections 14 that extend from a central section 16. Apertures 18 are positioned within the sections 14, 16 to receive screws 22. An upper edge 20 of the plate 12 has a curved orientation formed between the first and second sections 14. The plate 12 is mounted with the curved section 20 centered below the exterior occipital protuberance P of the skull S, and aligned along the superior nuchal line (labeled N). This placement positions the apertures 18 and screws 22 along a thickened section of the occiput that assures a stronger mount.

The fixation system 10 shown in FIGS. 1 and 2 also includes a pair of rod couplings, generally designated by the number 30. The rod couplings 30 are of the type permitting multi-axial positioning as is shown in U.S. Pat. No. 6,485,491, which is hereby incorporated by reference in its entirety. The rod coupling 30 comprises a saddle 32 within which a structural support rod 34 of the type shown in FIG. 2 is inserted. The rod 34 is coupled to the plate 12 to provide a rigid supporting structure that is fixed to the skull and/or vertebral members. The present invention is generally directed at various improvements to the coupling 30 that permits pivotal and rotational attachment of the support rod 34. The descriptions herein disclose embodiments of the improved couplings 30 as used with a plate 12 of an occipital fixation system 10, but the couplings 30 may be equally applicable to other spinal fixation devices used in the thoracic and lumbar regions of the spine. Other orthopedic applications where increased degrees of freedom for attaching support rods may also be applicable.

Figure 3:
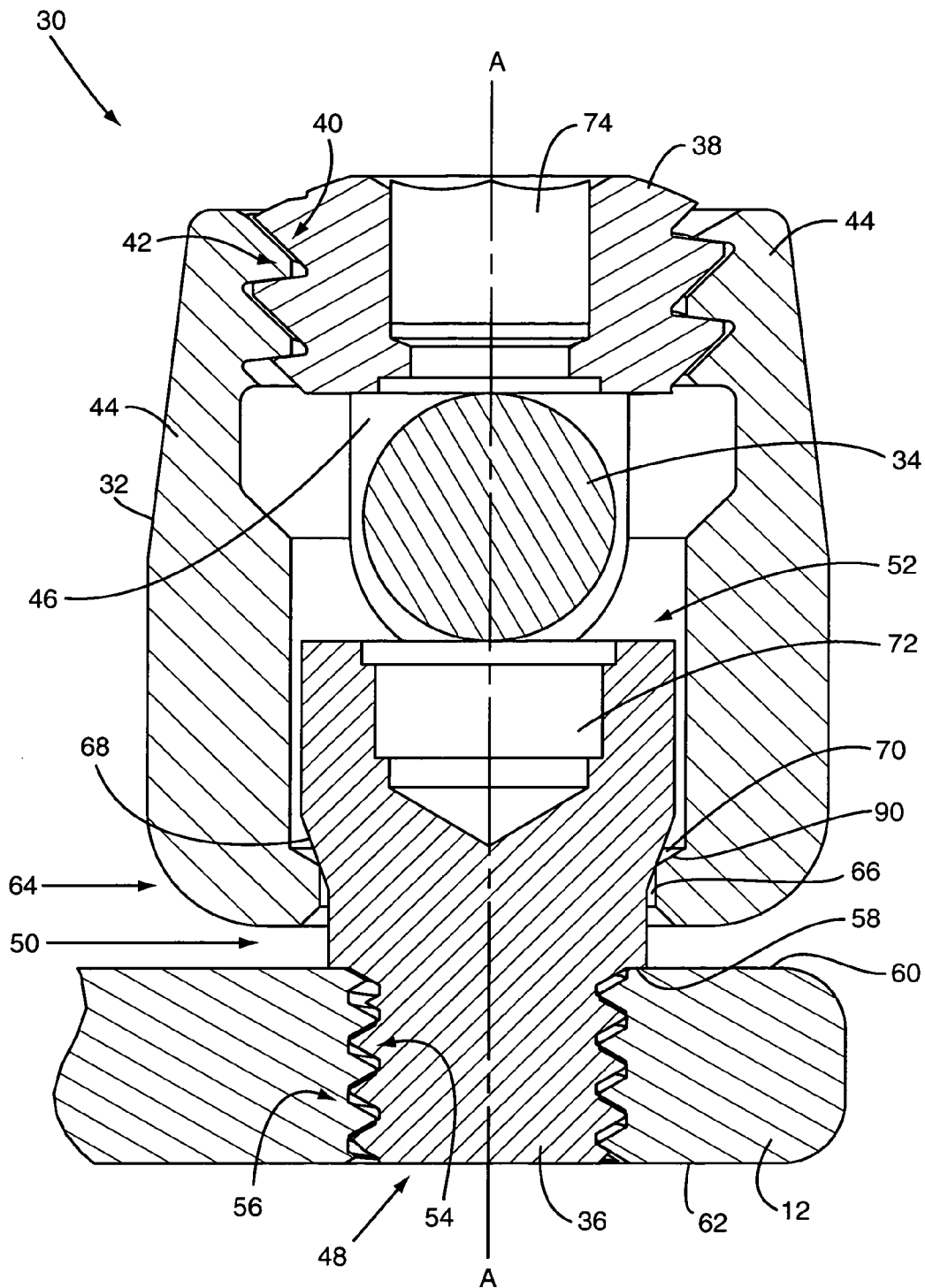
FIG. 3 is cross sectional view of a fixation system coupling according to one embodiment of the present invention.

Referring now to FIG. 3, a section view of one embodiment of the coupling 30 is shown. The coupling 30 permits axial rotation of the saddle 32 about axis A so that non-parallel rods 34 can be mounted to plate 12 in a configuration that accommodates the physiological anatomy of the patient. The coupling 30 also includes an anchor 36 and an engagement member 38. The anchor 36 may be generally subdivided into portions that include a threaded end 48, a neck 50, and a head 52. The threaded end 48 includes threads 54 that engage with a threaded aperture 56 in the plate 12. The engagement depth for the anchor 36 into the plate 12 is determined by length of the threaded end 48 that extends beyond a stop flange 58 that is positioned between the head 52 and the threaded end 48. In one embodiment, the threaded aperture 56 extends through the entire thickness of the plate 12 from the top surface 60 to the bottom surface 62. In one embodiment, the stop flange 58 abuts the top surface 60 of the plate 12. In other embodiments, the threaded aperture 56 may be a blind hole with a predetermined depth and the stop flange 58 may abut a counterbore or other recessed feature (not shown). In any case, the stop flange 58, threaded end 48, and threaded aperture 56 are dimensioned so that the threaded end 48 does not extend beyond the bottom surface 60 of the plate.

In one embodiment, the engagement member 38 is a setscrew having external threads 40 that mate with internal threads 42 that are formed in upright portions 44 of the saddle 32. The upright portions 44 extend upwardly from lower portion 64. The upright portions 44 form a channel 46 within which the rod 34 is inserted.

Figure 4:
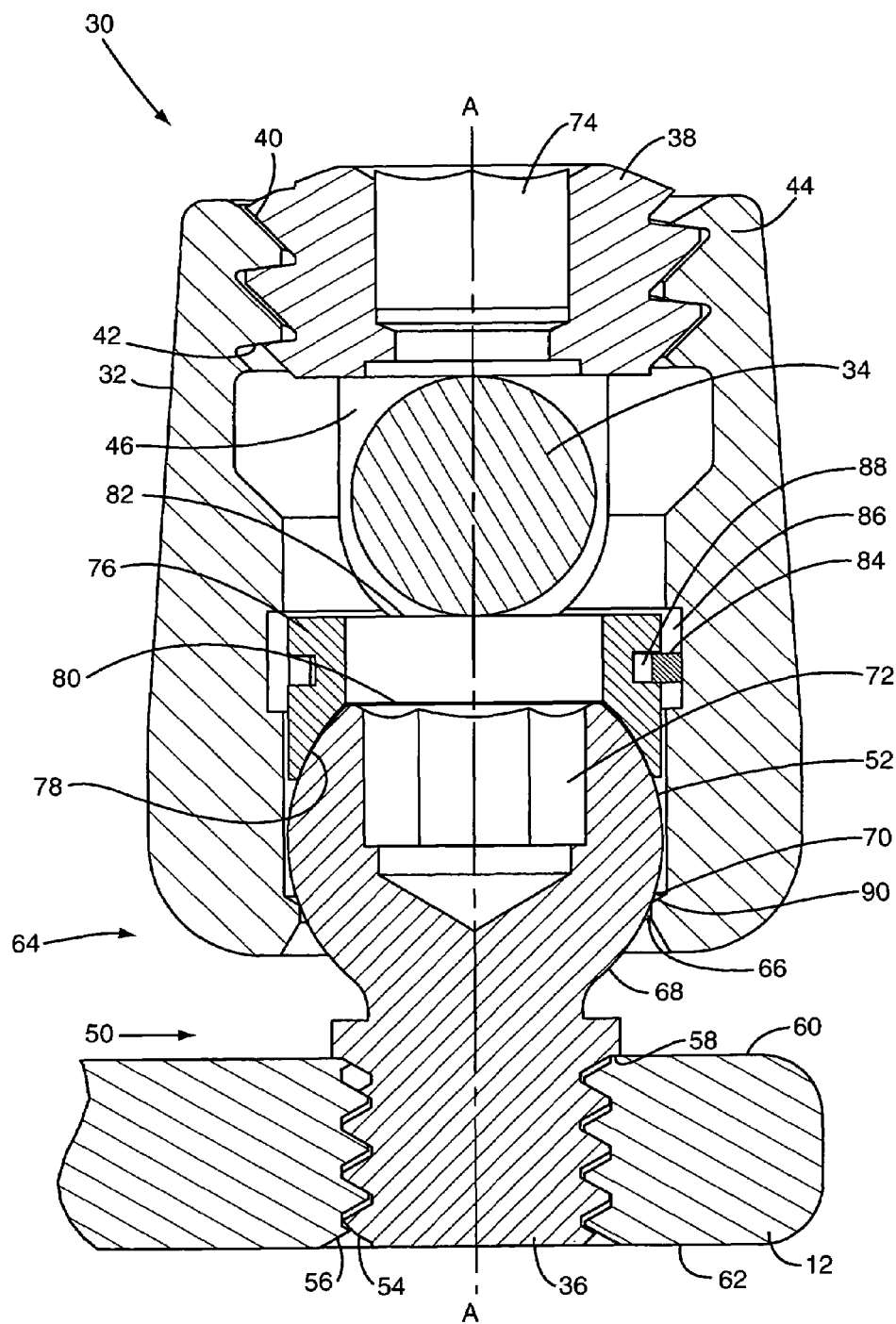
FIG. 4 is cross sectional view of a fixation system coupling according to one embodiment of the present invention.

An opening 66 in the lower portion is sized to accept the neck 50 of anchor 36. The opening 66 is smaller in width than the head 52 of anchor 36. With the anchor 36 inserted as shown in FIG. 3 and the saddle 32 captured between the head 52 of the anchor 36 and the plate 12, the saddle 32 is freely rotatable about axis A. As the setscrew 38 is threaded into contact with rod 34, the setscrew 38 applies a downward force on the rod 34. An equal, but opposite reactive force is generated on the upper portions 44 of the saddle 32 that acts to lift the saddle 32 into engagement with the head 52 of the anchor 36. A transition region 70 between the lower portion 64 and the upright portions 44 determines the amount of contact between the saddle 32 and anchor 36. In one embodiment, the transition region 70 and contact region 68 are tapered so as to create a substantially circular contact between the anchor 36 and saddle 32. In another embodiment as shown in FIG. 4, the contact region 68 is substantially spherical shaped. As FIG. 4 shows, the transition region 70 of the saddle 32 may retain the tapered shape shown in FIG. 3. In an alternative embodiment, the transition region may also be a spherical bearing surface to create a ball and socket type attachment between the anchor 36 and saddle 32. In another embodiment, the contact region 68 of anchor 36 and transition region 70 of saddle 32 are tapered at substantially the same angle so as to create a conical area of contact between the anchor 36 and saddle 32. In each of the above embodiments, the saddle 32 is advantageously pivotable about axis A. In the spherical embodiments, the saddle 32 is advantageously pivotable about multiple axes.

The embodiment of coupling 30 shown in FIG. 3 is attached to plate 12 in the following manner. The anchor 36 is first inserted into opening 66 of saddle 32. In one embodiment, the opening 66 in saddle 32 is a through-hole that extends through an otherwise solid lower portion 64. The anchor 36 is then threaded into the threaded aperture 56 in plate 12. The anchor 36 is threaded via a drive feature 72 that is of a type commonly known to those skilled in the art. Non-limiting examples of drive feature 72 include hex, Torx® square, and slotted drive mechanisms. The anchor 36 is inserted into plate 12 until stop flange 58 prevents additional engagement. The saddle 32 is then roughly rotated about axis A to accept rod 34. The rod 34 is inserted into channel 46 and then setscrew 38 is threaded into the threads 42 in upright portions 44. Setscrew 38 is also driven by a drive feature 74 that is of a type commonly known to those skilled in the art. The examples provided for drive feature 72 apply for drive feature 74 although the feature need not be the same for both the anchor 36 and setscrew 38.

Although the engaging member 38 has been described as embodying a setscrew, other designs may be used. As an alternative embodiment, the engaging member 38 may be a flexible, disc or cylindrical shaped device that is pushed into saddle 32 so as to engage retaining features in the upright portions 44 of saddle 32. Once locked into saddle 32, the engaging member applies a downward pushing force on rod 34 and a lifting force on saddle 32. Other embodiments performing these functions may be possible as well.

In an alternative embodiment of the saddle 32, the opening 66 may be a slotted feature in contrast to the aforementioned through-hole. Thus, the lower portion 64 of saddle 32 would be substantially u-shaped, with the slotted opening 66 sized to allow the saddle 32 to be inserted under the head 52 of the anchor 36 after the anchor 36 is inserted into plate 12.

In the embodiment shown in FIG. 4, an annular washer 76 may be incorporated for at least two reasons. First, the bottom side 78 of the washer 76 can be spherically shaped to match the shape of the head 52 of anchor 36. As the engaging member 38 is inserted into saddle 32, a downward force is imparted on rod 34 and subsequently on washer 76 and head 52. The matching surface 78 at the junction between washer 76 and head 52 provides multi-axial pivoting adjustability. A second reason for including washer 76 is to provide a larger surface area to support rod 34 from below. Where a spherical head 52 of anchor 36 is used as shown in FIG. 4, the top surface 80 of head 52 reduces in size compared to, for example, the embodiment shown in FIG. 3. Thus, the inclusion of washer 76 provides a more substantial surface 82 on which the rod 34 is placed.

In one embodiment, a retaining member such as c-clip 84 may be included with washer 76. The c-clip 84 is placed within an annular groove 88 around the perimeter of washer 76. Once the washer 76 is inserted into the saddle, the c-clip 84 resides within a saddle groove 86 located in the upright portions 44 of the saddle 32. The c-clip 84 loosely retains the washer in place within the saddle 32 and above the head 52 of anchor 36, but still permits multi-axial positioning of the saddle 32 relative to the anchor 36 and plate 12 until the engaging member 38 is inserted.

Figure 5:
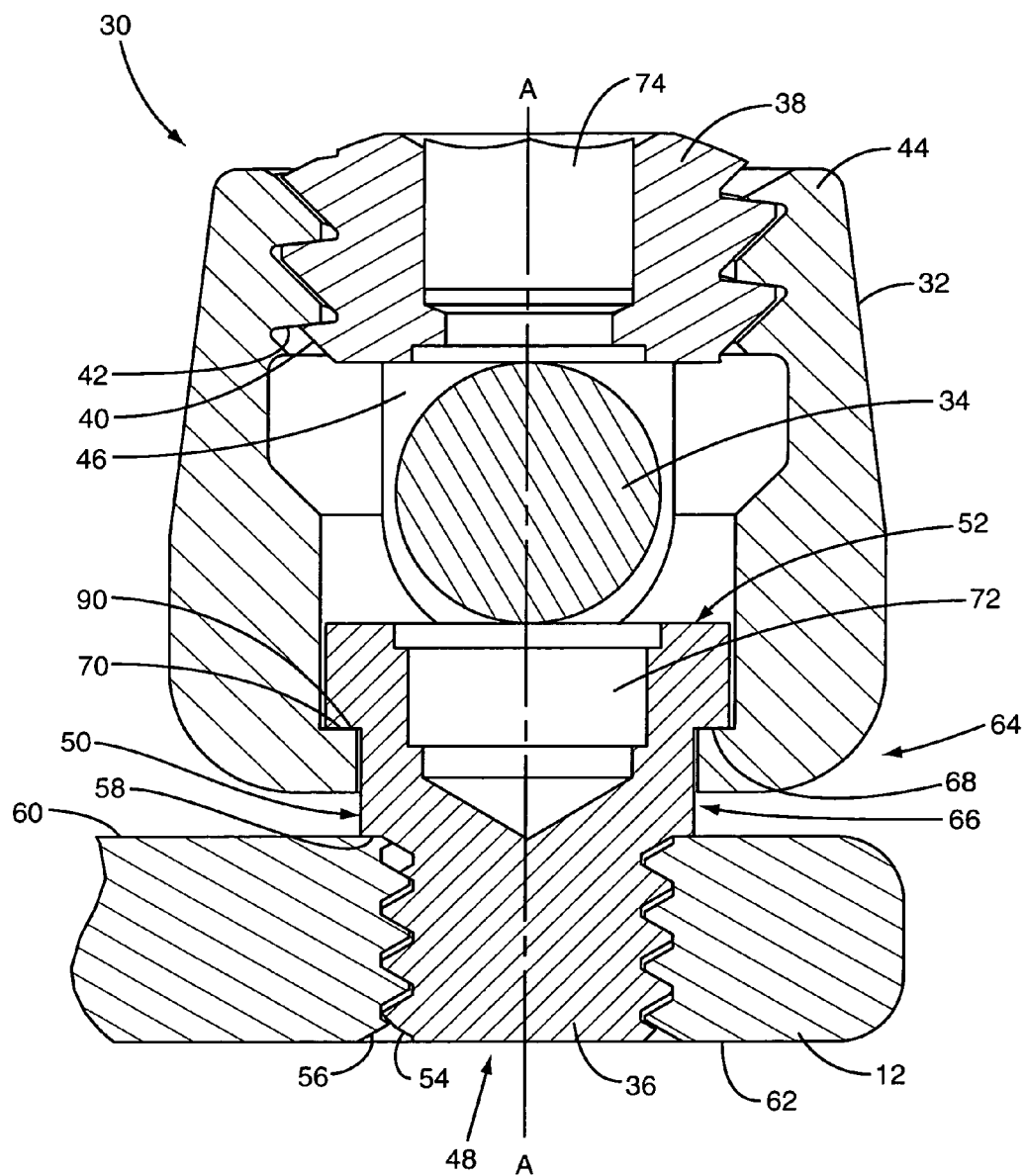
FIG. 5 is cross sectional view of a fixation system coupling according to one embodiment of the present invention.

In an alternative embodiment shown in FIG. 5, the contact region 68 on the underside of head 52 on anchor 36 is substantially horizontal. In the assembled state, where engaging member 38 is inserted in saddle 32, the horizontal contact region 68 abuts a substantially horizontal transition region 70 on saddle 32.

Figure 6:
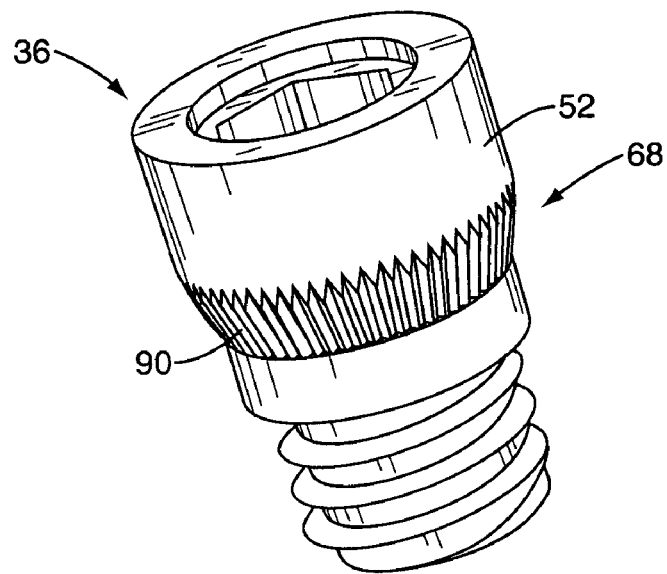
FIG. 6 is an upper perspective view of an anchor for use with a fixation system coupling according to one embodiment of the present invention.
Figure 7:
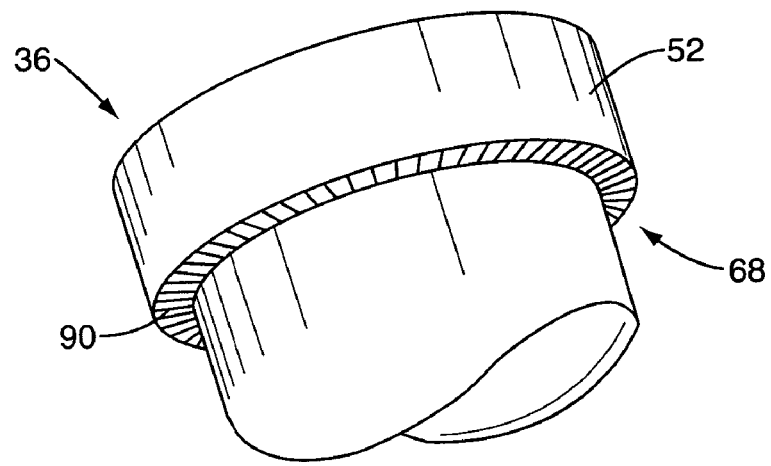
FIG. 7 is a lower partial perspective view of an anchor for use with a fixation system coupling according to one embodiment of the present invention.

The contact region 68 and transition region 70 of the various embodiments (see FIGS. 3-5) are substantially smooth. In other embodiments, the contact region 68 and transition region 70 have cooperating locking features that prevent axial rotation of the saddle 32 about axis A when the coupling is fully assembled. FIGS. 6 and 7 show examples of these locking features 90 on the contact region 68 of anchor 36. The anchor 36 shown in FIG. 6 corresponds to the embodiment shown in FIG. 3, while the anchor 36 shown in FIG. 7 corresponds to the embodiment shown in FIG. 5. In each embodiment, a series of spline-shaped locking features 90 are formed into the contact region 68 below head 52. Similarly shaped locking features 90 may be formed into the transition region 70 shown in the embodiments in FIGS. 3-5. The cooperating locking features 90 on contact region 68 and transition region 70 are generally out of contact with each other until the engaging member 38 is inserted into saddle 32. The lifting action (described above) imparted on saddle 32 that is caused by engaging member 38 further causes the locking features 90 to interface with one another. Thus, before the engaging member 38 is installed, the saddle 32 remains pivotable at least about axis A. However, once engaging member 38 is installed, thereby pulling the locking features 90 into contact with each other, the saddle 32 position is fixed.

In the embodiments shown in FIGS. 6 and 7, spline-shaped locking features 90 are shown. However, other embodiments incorporating different shapes for locking features 90 may be used. Some non-limiting examples include knurled surfaces, coarse, abrasive or frictional surface features and gear-type surfaces. In some embodiments, the locking feature 90 is formed on both the contact region 68 of anchor 36 and the transition region 70 of saddle 32. In other embodiments, the locking feature 90 is formed in only one of the contact region 68 or transition region 70. Also, as indicated, other embodiments might not incorporate the locking feature 90 at all.

Figure 8:
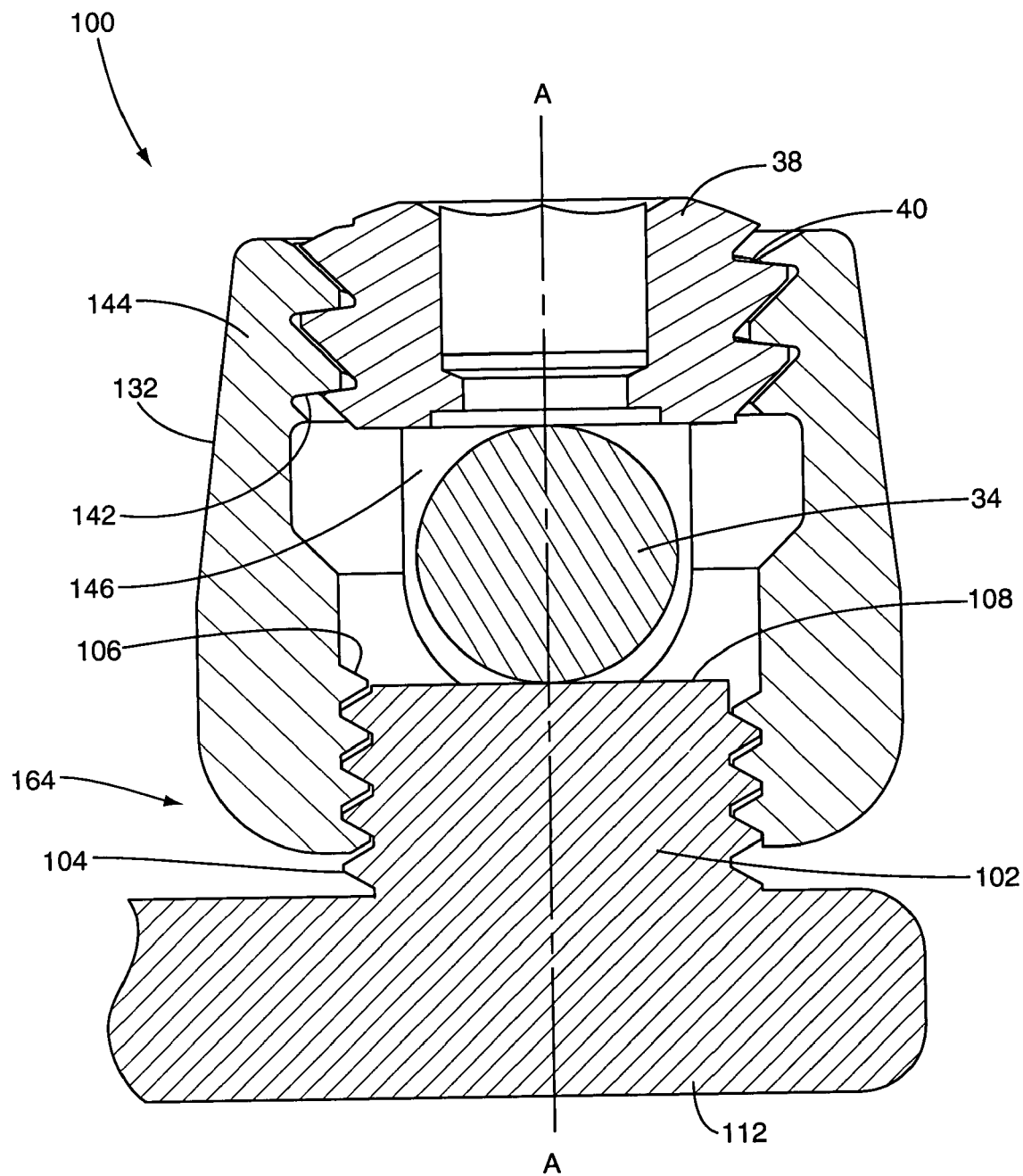
FIG. 8 is cross sectional view of a fixation system coupling according to one embodiment of the present invention.

Referring now to FIG. 8, an alternative embodiment of the coupling is designated generally by number 100. Coupling 100 works under many of the same principles heretofore described in conjunction with coupling 30. For example, the coupling 100 uses a saddle 132 comprising upright portions 144 that form a channel 146. An engaging member 38 that may be embodied as a setscrew is inserted into the channel and interfaces with retaining features in the inner walls of the upright portions 144. In one embodiment, the engaging member 38 has threads 40 that interface with internal threads 142 that are formed in the channel side of the upright walls 144.

One aspect of the coupling 100 that differs from coupling 30 is that a separate anchor is not used in coupling 100. Instead, a threaded stud 102 projects upwardly from the plate 112. The threaded stud 102 has external threads 104 formed around the exterior of the threaded stud 102. These external threads 104 are adapted to mate with internal threads 106 that are formed into the lower portion 164 of saddle 132. The mating threads 104, 106 permit axial rotation of the saddle 132 about axis A. The channel 146 in saddle 132 is advantageously deep enough that when rod 34 is placed within channel 146, the rod rests on the threaded stud 102. Thus, when engaging member 38 is inserted into the saddle 132, a downward force is applied to the rod 34 by engaging member 38. A reactive upward force is consequently applied to the rod 34 from the threaded stud 102. A separate reactive force is generated at the interface of threads 40, 142 and 106,104 so as to frictionally lock the coupling 100.

Figure 9:
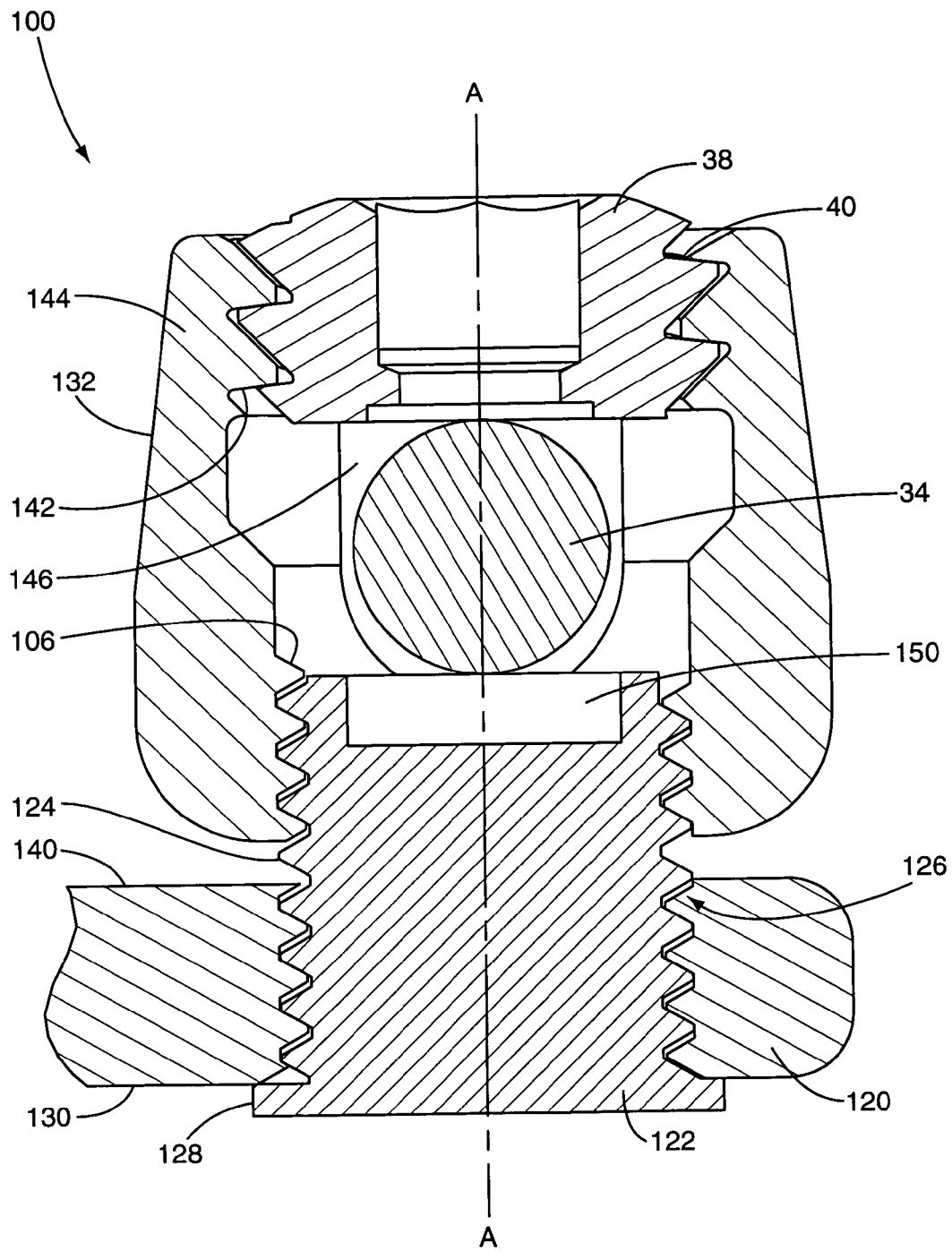
FIG. 9 is cross sectional view of a fixation system coupling according to one embodiment of the present invention.

In another embodiment of coupling 100 shown in FIG. 9, a separate threaded insert 122 is installed from a bottom side 130 of plate 120. The threaded insert 122 has external threads 124 that interface with mating threads 126 in plate 120. The threaded insert 122 has a flange 128 that limits the amount of engagement of threaded insert 122 into plate 120. In the embodiment shown in FIG. 9, the flange 128 abuts a bottom side 130 of plate 120. In alternative embodiments, the flange 128 may be recessed (as in a counterbore or other feature) so as not to extend beyond the bottom side 130 of the plate 120. In either case, the threaded insert projects upwardly above the top surface 140 of the plate 120. A drive feature 150 is provided in the threaded insert 122 at either the position shown or alternatively, at the flange end 128 of the threaded insert 122. The drive feature 150, similar to drive feature 72 described above, is of a type commonly known to those skilled in the art. Non-limiting examples of drive feature 150 include hex, Torx®, square, and slotted drive mechanisms. The threaded insert 122 is inserted into plate 120 until stop flange 128 prevents additional engagement.

A benefit to positioning the drive feature 150 in the location shown in FIG. 9 is the tendency for the area of the insert 122 around the feature 150 to deform under the clamping forces generated by engaging member 38. With the drive feature 150 positioned below the rod 34 as shown, the area of contact between the insert 122 and rod 34 is limited. As engaging member 38 is threaded into the saddle 132, the limited area of contact around the drive feature 150 is subjected to large compressive forces. The design of drive feature 150 and hardness of insert 122 may be advantageously selected so that the portion of the insert 122 surrounding the drive feature 150 is deformed slightly under these compressive forces. This deformation tends to further lock the rod 34 and help prevent rotation of the rod 34 and saddle 132 after assembly.

Once the threaded insert 122 is installed, the remainder of the coupling 100 may be assembled as in the embodiment shown in FIG. 8. The saddle 132, engaging member 38 and rod 34 shown in FIG. 8 advantageously remain unchanged in the embodiment shown in FIG. 9. The internal threads 106 in the lower portion 164 of saddle 132 interface with external threads 124 of the threaded insert 122. Engaging member 38 is inserted as described above to frictionally lock the coupling in place.

Figure 10:
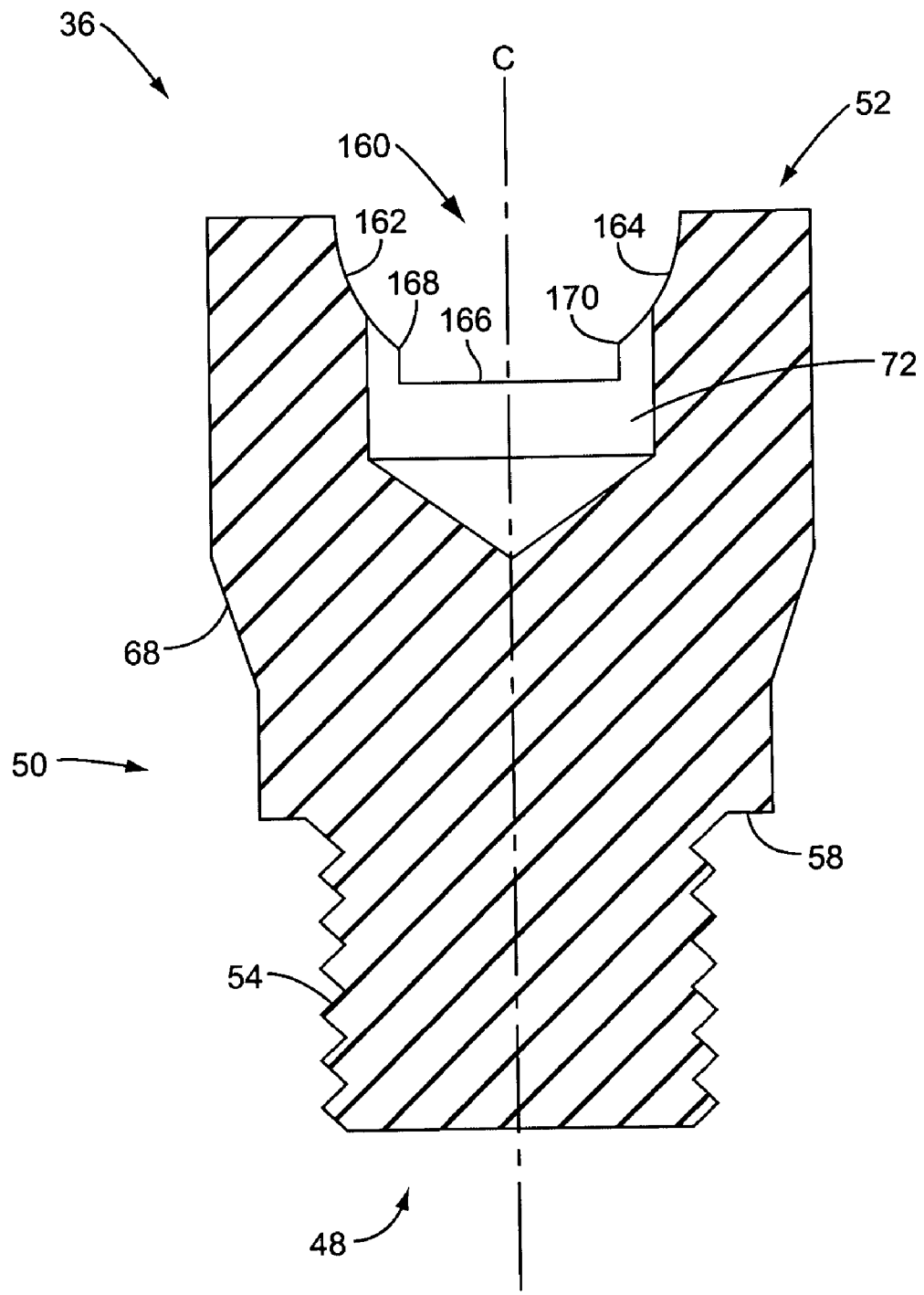
FIG. 10 is cross sectional view of an anchor for use with a fixation system coupling according to one embodiment of the present invention.

In the embodiments of coupling 30, 100 described above, the rod 34 has been supported from below by a substantially flat surface. This configuration allows rods 34 of varying diameters to be installed within the coupling 30, 100. Alternatively, a support feature 160 shown in FIG. 10 may be included in each of the embodiments heretofore described. For example, the support feature 160 is shown in FIG. 10 incorporated into the anchor 36 that is part of the coupling 30 shown in FIG. 3. Similarly, the support feature 160 can be implemented in any of the other anchor embodiments or in the washer 76 of FIG. 4, the threaded stud 102 of FIG. 8, or the threaded insert 122 of FIG. 9. The support feature 160 includes a pair of concave surfaces 162, 164 that are mirrored about the central axis C of the anchor 36. A slot 166 is disposed between the concave surfaces 162, 164. The concave surfaces 162, 164 may be advantageously sized to substantially match the diameter of rod 34. Alternatively, the concave surfaces 162, 164 may be larger than the diameter of rod 34. When then anchor 36 shown in FIG. 10 is used in the coupling 30 of FIG. 3, the rod 34 is clamped in place by three contact points. The rod is supported from below by concave surfaces 162 and 164 or by edges 168 and 170. The rod 34 is clamped from above by the bottom of engaging member 38.

The present invention may be carried out in other specific ways than those herein set forth without departing from the scope and essential characteristics of the invention. For example, while the various coupling embodiments have been described in the context of attaching a rod to an occipital fixation plate, the couplings may be equally applicable to other fixation devices, including bone screws or pedicle screws. The present embodiments are, therefore, to be considered in all respects as illustrative and not restrictive, and all changes coming within the meaning and equivalency range of the appended claims are intended to be embraced therein.

What is claimed is:

1. An orthopedic fixation system for attachment of a rod comprising:
    a plate having a top surface and a bottom surface, the plate having at least one threaded
    aperture extending at least partially between the top surface and the bottom surface;
    an elongated anchor comprising:
    a first threaded end that mates with the threaded aperture to attach the anchor to the plate,
    a mount at a second end opposite the first end, and
    a flange extending outward at a position between the threaded end and the mount and having a width greater than the threaded aperture and a bottom surface of the flange being in contact with the top surface of the plate when the anchor is fully mounted to the plate; and
    a saddle attached to the mount, the saddle comprising upwardly extending arms spaced a distance apart to form a channel, the saddle being pivotally attached to the anchor to receive a rod within the channel at a variety of positions relative to the plate.

2. The orthopedic fixation system of claim 1 wherein the mount has a substantially spherical shape and the saddle has a bearing surface to accept the substantially spherical shape.

3. The orthopedic fixation system of claim 1 wherein a distance between the first threaded end and a bottom surface of the flange is less than or equal to the distance between the top surface and the bottom surface of the plate.

4. The orthopedic fixation system of claim 1 wherein the aperture extends through the thickness of the plate.

5. An orthopedic fixation system for attachment of a rod comprising:
    a plate having a top surface and a bottom surface, the plate having at least one threaded aperture extending at least partially between the top surface and the bottom surface;
    an anchor having a first threaded section, a head, and a flange positioned therebetween, the first threaded section engaged with the threaded aperture with a bottom surface of the flange contacting the top surface of the plate and the head extending above the top surface; and
    a saddle having a plurality of upright portions that define a channel that receives a rod through the saddle member, and a lower portion that cooperates with the head to allow multi-axial movement of the saddle relative to the plate.

6. An orthopedic fixation system:
    a plate having at least one aperture;
    an anchor having a first end positioned within the aperture and a plurality of first locking features on the surface of the anchor;
    a saddle having a plurality of upright portions that define a channel and an opening positioned on a lower section below the channel, the saddle further comprising a plurality of second locking features; and
    an engagement member sized to fit within the channel and engage the plurality of upright portions,
    engagement of the engagement member within the plurality of upright portions and with a rod causes upward movement of the saddle relative to the anchor to engage the plurality of first and second locking features.

7. The orthopedic fixation system of claim 6 wherein the anchor is a screw having threads on a first end that engage threads within the aperture of the plate.

8. The orthopedic fixation system of claim 6 wherein the engagement member is a setscrew having external threads that engage internal threads on the plurality of upright portions.

9. The orthopedic fixation system of claim 6 further comprising a rod positioned between the engagement member and the anchor.

10. The orthopedic fixation system of claim 6 wherein the upright portions of the saddle extend upwards from the lower section to define a substantially u-shaped channel.

11. The orthopedic fixation system of claim 6 wherein the opening is a hole positioned entirely within the lower section and surrounded in all directions by the plurality of second locking features.

12. The orthopedic fixation system of claim 6 wherein the lower section is substantially u-shaped and the opening is a slot.

13. An orthopedic fixation system comprising:
    a plate;
    a saddle having a lower section and spaced apart arms extending upward from the lower section;
    an opening positioned within the lower section of the saddle;
    an anchor having a neck and head, the neck extending upward from the plate through the opening and the head positioned between the arms; and
    an engagement member positioned between the arms and above the head;
    engagement of the engagement member within the plurality of arms and with a rod causes upward movement of the saddle relative to the anchor causing contact between the anchor and the lower section, at least one of the anchor and the lower section including locking features to prevent rotational movement of the saddle relative to the anchor.

14. The orthopedic fixation system of claim 13 wherein the head is wider than the neck.

15. The orthopedic fixation system of claim 14 wherein the neck is curved.

16. The orthopedic fixation system of claim 14 wherein the neck is tapered.

17. The orthopedic fixation system of claim 16 wherein the locking features are positioned on the tapered neck.

18. The orthopedic fixation system of claim 13 wherein the locking features are positioned on a lower side of the head.

19. The orthopedic fixation system of claim 13 wherein the head is larger than the opening to limit the extent of upward movement of the saddle relative to the anchor.

20. The orthopedic fixation system of claim 13 wherein the locking features are on both the anchor and the saddle.

21. The orthopedic fixation system of claim 13 wherein the opening is wider than the neck to allow axial rotation of saddle about the anchor.

22. The orthopedic fixation system of claim 13 wherein the locking features are splines.

23. The orthopedic fixation system of claim 13 wherein the locking features are knurls.

24. The orthopedic fixation system of claim 13 wherein the locking features are frictional features.

25. The orthopedic fixation system of claim 13 wherein the head has a concave support feature to support the rod.

26. An orthopedic fixation system for attachment of a rod comprising:
a plate;
a saddle having a lower section and spaced apart arms extending upward from the lower section, the spaced apart arms forming a channel into which the rod is positioned;
an opening positioned within the lower section of the saddle;
an anchor having a neck and head, the neck extending upward from the plate and extending through the opening, and the head positioned between the arms, the rod being placed on a top portion of the head;
an engagement member positioned between the arms and above the rod;
the engagement of the engagement member within the arms causes a downward force on a rod and upward movement of the saddle relative to the anchor.

27. An orthopedic fixation system for attachment of a rod comprising:
a plate having a top surface and a bottom surface, the plate having at least one threaded aperture extending at least partially between the top surface and the bottom surface;
an elongated anchor comprising:
a threaded section that mates with the threaded aperture to attach the anchor to the plate,
a mount, and
a flange extending outward from a centerline and having a width greater than the threaded aperture and being in contact with the plate when the anchor is fully mounted to the plate, the threaded section disposed so as not to extend beyond the bottom surface of the plate; and
a saddle attached to the mount, the saddle comprising upwardly extending arms spaced a distance apart to form a channel, the saddle being pivotally attached to the anchor to receive a rod within the channel at a variety of positions relative to the plate.

28. An orthopedic fixation system:
a plate having at least one aperture;
an anchor having a first end positioned within the aperture and a second end extending upward above the plate;
a saddle having a plurality of upright portions that define a channel and an opening positioned on a lower section that connects with the anchor at a point above the plate; and
an engagement member sized to fit within the channel and engage the plurality of upright portions,
engagement of the engagement member within the plurality of upright portions and with a rod causes upward movement of the saddle relative to the plate.

29. An orthopedic fixation system comprising:
a plate;
a saddle having a lower section and spaced apart arms extending upward from the lower section;
an opening positioned within the lower section of the saddle;
an anchor having a neck and head, the neck extending upward from the plate through the opening and the head positioned between the arms; and
an engagement member positioned between the arms and above the head;
engagement of the engagement member within the plurality of upright portions and with a rod causes upward movement of the saddle relative to the anchor.

30. The orthopedic fixation system of claim 29 wherein the head is wider than the neck.

31. The orthopedic fixation system of claim 30 wherein the head is larger than the opening to limit the extent of upward movement of the saddle relative to the anchor.

32. The orthopedic fixation system of claim 29 wherein the opening is wider than the neck to allow axial rotation of saddle about the anchor.

33. An orthopedic fixation system for attachment of a rod comprising:
a plate having a top surface and a bottom surface, the plate having an aperture extending through the thickness of the plate between the top surface and the bottom surface;
an elongated anchor comprising:
a first end that mates with the aperture to attach the anchor to the plate, and a mount at a second end opposite the first end, and
a saddle attached to the mount, the saddle comprising upwardly extending arms spaced a distance apart to form a channel, the saddle being pivotally attached to the anchor to receive a rod within the channel at a variety of positions relative to the plate.

34. The orthopedic fixation system of claim 33 wherein the mount has a substantially spherical shape and the saddle has a bearing surface to accept the substantially spherical shape.

35. The orthopedic fixation system of claim 33 wherein the anchor is deformed against the rod to further support the rod.

36. An orthopedic fixation system for attachment of a rod comprising:
a plate having a top surface and a bottom surface, the plate having at least one threaded aperture extending at least partially between the top surface and the bottom surface;
an anchor having a first threaded section and a head, the first threaded section engaged with the threaded aperture from the top surface and extending through the threaded aperture no farther than the bottom surface, and the head extending above the top surface; and
a saddle having a plurality of upright portions that define a channel that receives a rod through the saddle member, and a lower portion that cooperates with the head to allow multi-axial movement of the saddle relative to the plate.

37. An orthopedic fixation system:
a plate having at least one aperture;
an anchor having a first end positioned within the aperture and a plurality of first locking features on the surface of the anchor;
a saddle having a plurality of upright portions that define a channel and an opening positioned on a lower section below the channel, the saddle further comprising a plurality of second locking features; and
an engagement member sized to fit within the channel and engage the plurality of upright portions,
engagement of the engagement member within the plurality of upright portions causes upward movement of the saddle relative to the anchor to engage the plurality of first and second locking features.

* * * * *